(12) United States Patent
Boss et al.

(10) Patent No.: US 7,116,416 B1
(45) Date of Patent: *Oct. 3, 2006

(54) THERMO-ELECTRICALLY COOLED SURFACE ENHANCED RAMAN SPECTROSCOPY SENSOR SYSTEM

(75) Inventors: Pamela A. Boss, San Diego, CA (US); Stephen H. Lieberman, La Mesa, CA (US); Leonard J. Martini, San Diego, CA (US); Gregory W. Anderson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/136,765

(22) Filed: May 24, 2005

Related U.S. Application Data

(62) Division of application No. 10/133,705, filed on Apr. 26, 2002.

(51) Int. Cl.
   *G01J 3/44* (2006.01)

(52) U.S. Cl. .................................... 356/301

(58) Field of Classification Search ............... 356/301
    See application file for complete search history.

(56) References Cited

U.S. PATENT DOCUMENTS

| 4,886,358 | A | * | 12/1989 | Pellenbarg et al. | .......... 356/301 |
| 6,025,202 | A | * | 2/2000 | Natan | .......... 356/301 |
| 6,770,488 | B1 | * | 8/2004 | Carron et al. | .......... 356/301 |

* cited by examiner

*Primary Examiner*—Hwa (Andrew) Lee
*Assistant Examiner*—Kara Geisel
(74) *Attorney, Agent, or Firm*—Andrew J. Cameron; Michael A. Kagan; Peter A. Lipovsky

(57) ABSTRACT

A sensor system employs a thermo-electrically cooled surface enhanced Raman (SERS) structure that is positioned in a sample chamber. Gas or vapor that may contain an analyte of interest is introduced into the sample chamber so that the analyte may come into contact with the SERS structure. The SERS structure may be cooled to facilitate condensation of selected analytes onto the SERS structure. When in contact with each other, the analyte and SERS structure may be optically stimulated by an optical excitation signal to produce a unique spectral response that may be detected by a spectroanalysis system. The spectral response then may be correlated to a specific analyte, i.e., identified.

12 Claims, 4 Drawing Sheets

THERMO-ELECTRICALLY COOLED SURFACE ENHANCED RAMAN SPECTROSCOPY SENSOR SYSTEM

CROSS REFERENCE TO RELATED APPLICATIONS

This is a divison of non-provisional U.S. patent application Ser. No. 10/133,705 by Pamela A. Boss et. al, filed Apr. 26, 2002, now pending, hereby incorporated by reference.

FEDERALLY-SPONSORED RESEARCH AND DEVELOPMENT

The THERMO-ELECTRICALLY COOLED SURFACE ENHANCED RAMAN SPECTROSCOPY SENSOR SYSTEM is assigned to the United States Government and is available for licensing for commercial purposes. Licensing and technical inquiries should be directed to the Office of Patent Counsel, Space and Naval Warfare Systems Center, San Diego, Code 20012, San Diego, Calif., 92152; telephone (619)553-3001, facsimile (619)553-3821.

BACKGROUND

The present invention generally relates to the field of Raman spectroscopy, and more particularly, to a sensor for detecting chemicals both in gas and liquid environments using surface enhanced Raman spectroscopy whereby any Raman scattering due to excitation of the optical elements of the sensor are minimized.

Raman spectroscopy is an emission technique that involves inelastic scattering of incident laser energy and results in spectral peaks that are frequency shifted from the incident energy. The Raman bands arise from changes in polarizability in a molecule during vibration. As a result, virtually all organic molecules display a characteristic Raman emission. Therefore, a Raman sensor would not be limited to a specific class of molecules as is the case for a laser induced fluorescence (LIF) sensor. Raman spectrometry allows the fingerprinting of species present and is structurally specific. The inherently high resolution of Raman spectra often permits the analysis of several components in a mixture simultaneously.

The advent of inexpensive, portable Raman spectrometers has seen renewed interest in the area of Raman spectrometry. This new generation of spectrometers employs fiber-optic probes, holographic notch filters for rejection of the Rayleigh line, a single grating monochromator, and a charge coupled device (CCD) detector for multichannel detection. These spectrometers contain a minimum of optical components as compared to conventional Raman instrumentation resulting in a high data throughput; and, once coupled to a laser and spectrometer, optical-fiber probes require no further alignment.

Despite the advantages of Raman spectroscopy over other spectroscopic techniques and the technological advances in the area of Raman spectrometry, Raman spectroscopy is, inherently, an insensitive technique. To achieve detection limits in the low ppm range would require either the use of a multiple pass cell or long acquisition times. In the 1970s, it was discovered that Raman scattering from molecules adsorbed on such noble metals as silver, copper, and gold can be enhanced by as much as 106 to 107. This phenomenon, called surface enhanced Raman spectroscopy (SERS), is still not understood despite intensive theoretical and experimental research. It is believed that more than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process. However, the sensitivity of the technique as well as its exceptional spectral selectivity has made SERS attractive for a broad range of analytical applications. SERS can be used for trace organic analysis and as a detection method in gas chromatography, liquid chromatography, and thin layer chromatography. Electrochemical SERS and SERS of chemically modified surfaces have been used to detect aromatic compounds and chlorinated hydrocarbons, organic contaminants of environmental concern, in the ppm concentration range.

There are many applications in which detection of particular chemical species or analytes is desirable, as for example, hydrocarbons that may be present in ground water, toxic vapors in industrial environments, explosives, metal ions, narcotics, toxic anions, and chemical warfare agents.

SERS is a very sensitive technique, but requires intimate contact between the SERS active surface and the analyte. This, in turn, requires that the sample be brought inside a chamber for analysis. However, there are practical problems in performing a SERS analysis that include: a) getting the sample inside a chamber; and b) purging the sample from the chamber. Therefore, a need exists for a system that overcomes the above-referenced problems.

SUMMARY

The present invention is a sensor system that employs a thermo-electrically cooled surface enhanced Raman (SERS) structure that is positioned in a sample chamber. Gas or vapor that may contain an analyte of interest is introduced into the sample chamber so that the analyte may come into contact with the SERS structure. The SERS structure may be cooled to facilitate condensation of selected analytes onto the SERS structure. When in contact with each other, the analyte and SERS structure may be optically stimulated by an optical excitation signal to produce a unique spectral response that may be detected by a spectroanalysis system. The spectral response then may be correlated to a specific analyte, i.e., identified.

The present invention includes a source for providing an inert gas; a manifold having a semipermeable membrane for separating moisture from an analyte wherein the analyte and the inert gas mix to create a gas mixture; a chamber body having a sample chamber for receiving the gas mixture; a SERS structure is positioned in the sample chamber; an optical energy source for generating an optical excitation signal that irradiates the SERS structure; and a spectroanalysis system for detecting optical emissions generated in response to the SERS structure being irradiated by the optical excitation signal when the analyte is in contact with the SERS structure. The analyte may be selected from the group that includes benzene, toluene, ethylbenzene, MTBE, TNT, RDX, cocaine, heroin, saran, xylene, mustard gas, and chlorinated solvents. Heating the semipermeable membrane under the supervision of a controller may be employed to increase the volatility of the analyte, and thereby enhance its detection. The invention may be used to detect analytes that are in both gaseous, liquid, and even soil environments.

Different analytes condense at different temperatures. Cooling the temperature of the SERS structure facilitates condensation of selected analytes that may be present in the sample chamber so that they may condense onto the SERS structure. When in contact with each other, the analyte and SERS structure may be optically stimulated by the optical excitation signal to produce a unique spectral response that may be detected by the spectroanalysis system and then correlated to a particular analyte. For example, vapor condensation of benzene occurs at 15° C., toluene at 9° C., and MTBE at −5° C.

The invention may also be characterized as a method for identifying an analyte of interest that may be present in gas, liquid, or soil environments. The method includes the steps of: a) mixing a sample gas with an inert gas to create a gas mixture; b) contacting a self-assembled monolayer of a SERS structure with the inert gas; c) irradiating the self-assembled monolayer with optical excitation energy for stimulating a SERS optical emission signal if the sample gas contains an analyte that is in contact with the self-assembled monolayer; and d) determining the identity of the analyte from the SERS optical emission signal. The optical excitation energy may be a coherent optical signal having a wavelength in the range of about 633 to 852 nm. Such longer wavelengths are in the near-infrared range and provide a better SERS response, i.e., greater output of the optical emission signal. Also, longer wavelengths of optical excitation energy reduces fluorescence interference with the optical emission signal. The self-assembled monolayer may be cooled to condense any analyte present in the gas mixture. Moreover, the inert gas may be drawn through a semipermeable membrane that may be heated to vaporize any analyte present in the liquid environment. The method may further include the step of removing moisture from the gas mixture that would otherwise inhibit generation of the optical emission signal.

These and other advantages of the invention will become more apparent upon review of the following specification, including the claims, and the accompanying figures.

BRIEF DESCRIPTION OF THE DRAWINGS

Throughout the drawings, like elements are referenced using like designations.

DETAILED DESCRIPTION

The present invention is a sensor system that employs a thermo-electrically cooled surface enhanced Raman (SERS) structure that is positioned in a sample chamber. Gas or vapor that may contain an analyte of interest is introduced into the sample chamber so that the analyte may come into contact with the SERS structure. The SERS structure may be cooled to facilitate condensation of selected analytes onto the SERS structure. When in contact with each other, the analyte and SERS structure may be optically stimulated by an optical excitation signal to produce a unique spectral response that may be detected by a spectroanalysis system. The spectral response then may be correlated to a specific analyte, i.e., identified.

Figure 1:
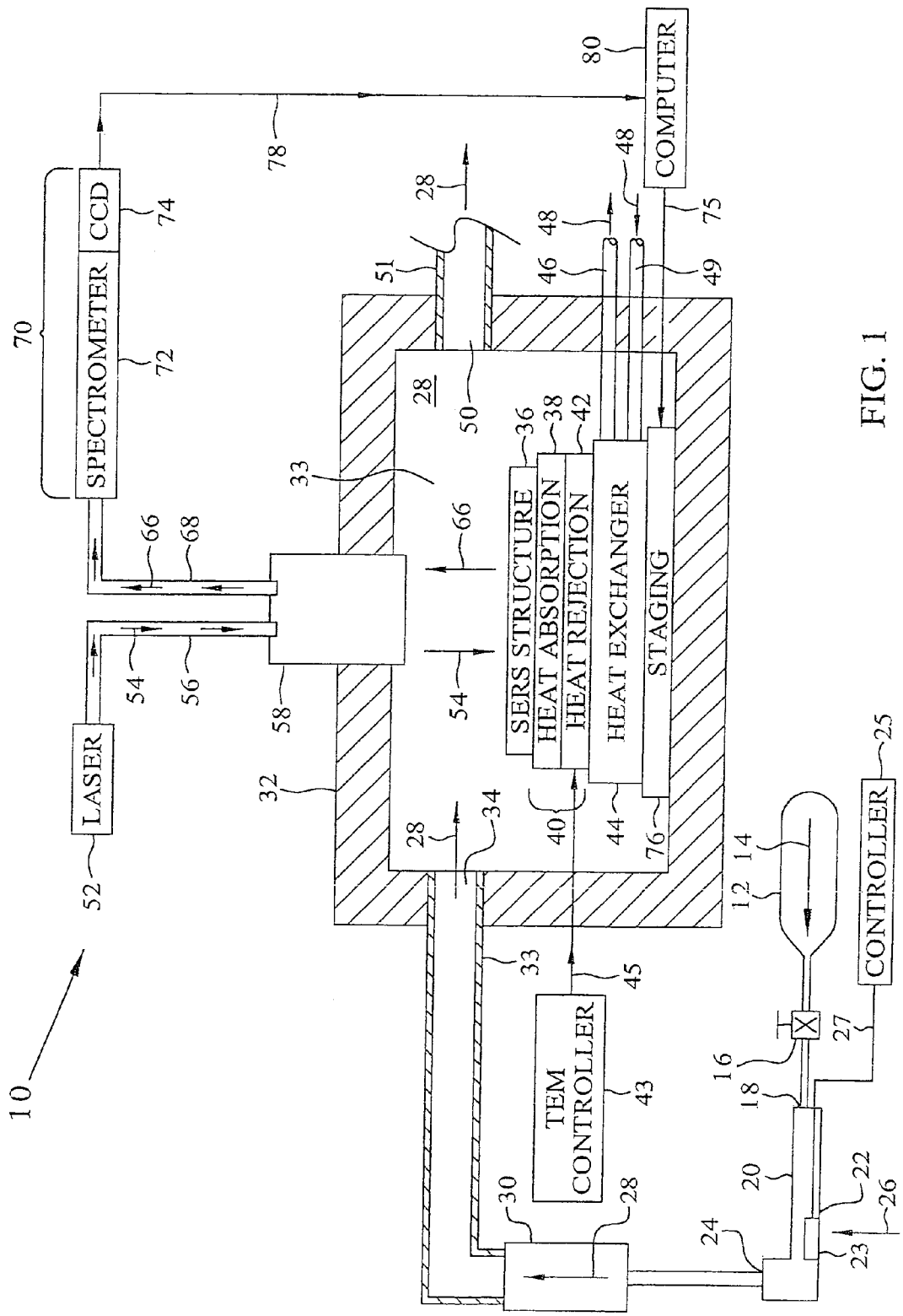
FIG. 1 is a block diagram of a thermo-electrically cooled surface enhanced Raman spectroscopy sensor system that embodies various features of the present invention.

The invention is described with reference to FIG. 1 wherein there is shown sensor system 10 which includes a gas source 12 for providing an inert gas 14 such as diatomic nitrogen (N2) under the control of valve 16 through input port 18 into manifold 20. Manifold 20 also includes an analyte input port 22 in which a semipermeable membrane 23 is mounted, and an output port 24. Negative pressure created as inert gas 14 flows over analyte input port 22 and through manifold 20 causes analyte 26, which may be a gas or a vapor, to be drawn into manifold 20 through semipermeable membrane 23. Analyte 26 and inert gas 14 mix to create sample gas mixture 28 in manifold 20. Semipermeable membrane 23 may be immersed in a gas, liquid, or soil environments, and minimizes the introduction of moisture and debris into manifold 20. Semipermeable membrane 23 may be heated under the supervision of controller 25 via signal line 27 in order to increase the volatility of organic analytes 26, especially when semipermeable membrane 23 is in contact with liquid environments such as aqueous or saturated soil environments. Semipermeable membrane 23 and controller 25 may be implemented as Geoprobe Systems Part Nos. MP3512 and MP2500, respectively. Examples of analytes 26 detectable by sensor system 10 are provided by way of example in TABLE 1 which provides, by way of example, a list of examples of thiols and analytes that may be detected using such a thiol coating 122 (FIG. 6) in SERS structure 36. However, TABLE 1 is not to be considered exhaustive of the types of analytes that may be detected by system 10. For example, the present invention may also be used for detecting blister agents, such as mustard gas.

TABLE 1

| Thiol Type | Analytes |
| --- | --- |
| 1-propanethiol | Benzene, toluene, ethylbenzene, methyl tetrabutyl ether (MTBE), xylene, and chlorinated solvents |
| cysteamine hydrochloride | trinitrotoulene (TNT), explosives such as cyclotrimethylenetrinitramine (RDX) |
| 2-propanethiol | cocaine, heroin, saran |

Next, gas mixture 28 flows out of output port 24 and through desiccant chamber 30 which removes moisture from gas mixture 28 that may have passed through semipermeable membrane 23. After passing through desiccant chamber 30, gas mixture 28 flows through tube 33 to fill sample chamber 33 of chamber body 32 via input port 34. Gas mixture 28 is vented from sample chamber 33 through outlet tube 51 via output port 50. By way of example, chamber body 32 may be made of Delrin®, Nylon®, Teflon®, and other materials that are generally inert to analyte 26. Desiccant chamber 30 may be implemented as a molecular sieve water vapor trap, such as Supelco Part No. 20618.

Sample chamber 32 includes a SERS structure 36 that is mounted to the heat absorption, or cooling side 38 of thermoelectric (TEM) cooler 40, which also includes a heat rejection side 42 for rejecting heat absorbed from the SERS structure 36 by cooling side 38. TEM cooler 40 operates under the supervision of TEM controller 43 via signal line 45. Different analytes condense at different temperatures. For example, vapor condensation of benzene occurs at 15°

C., toluene at 9° C., and MTBE at −5° C. Therefore, controlling the temperature of TEM cooler 40, and hence, SERS structure 36 allows specific analytes to be condensed onto SERS structure 36. Examples of a suitable TEM cooler 40 and controller 43 for use in system 10 are available from Melcor. Different analytes 26 detectable by sensor system 10 condense at different temperatures. Therefore, controlling the temperature of SERS structure 36 facilitates condensation of selected analytes 26 that may be present in sample chamber 33 so that a particular analyte 26, if present in chamber 33, may contact SERS structure 36 and be detected. SERS structure 36 may be adhesive bonded to TEM cooler 38 using a thermal grease, such as Melcor Part No. 2TG-001. The fabrication of SERS structure 36 is described further herein.

The heat rejection side 42 of thermoelectric cooler 38 is mounted to heat exchanger 44, which may be a gas or liquid heat exchanger. Heat exchanger 44 transfers heat energy absorbed from heat rejection side 42 of thermoelectric cooler 38 out of sample chamber 33. By way of example, heat exchanger 44 may have a fluid inlet tube 49 for receiving fluid 48 that is relatively cool for absorbing heat energy from the heat rejection side 42 of TEM cooler 38, and an outlet tube 46 through which the heated fluid 48 flows out of the heat exchanger 44. Fluid 48 may be either a gas, such as a air, or a liquid, such as water. However, it is to be understood that fluid 48 may include gases and liquids other than those specifically identified herein. SERS structure 36 is immersed within and in intimate contact with gas mixture 28 when gas mixture 28 fills sample chamber 33.

An optical energy source such as laser 52 generates a monochromatic and coherent excitation light signal 54 that is injected into optical excitation fiber 56 that is optically coupled to optical module 58. Optical module 58 directs and focuses excitation light signal 54 received from optical excitation fiber 56 to irradiate SERS structure 36, and also filters out any Raman emissions that may result from excitation light signal 54 propagating through optical fiber 56. An example of an optical module suitable for use in the present invention is commercially available from InPhotonics, Inc. and simply known as a RamanProbeÔ The irradiation of SERS structure 36 by excitation light signal 54 in the presence of analyte 26 mixed in gas mixture 28 causes the generation of surface enhanced Raman scattering (SERS) optical emissions 66. Preventing or minimizing moisture from entering sample chamber 32 is important because any water, whether liquid, vapor, or solid, that comes into contact with SERS structure 36 could obscure optical emissions 66. Optical module 58 includes a lens (not shown) for gathering and directing some of such SERS optical emissions 66 into optical fiber 68. Another function of optical module 58 is to prevent excitation light 54 from entering optical fiber 68, and thereby prevent the stimulation of Raman emissions therein. Optical emissions 66 are propagated via optical fiber 58 to spectroanalysis system 70. By way of example, excitation light signal 54 preferably has a wavelength in the range of about 633 to 852 nm. Longer wavelengths of excitation light signal 54 in the near-infrared range provide a better SERS response, i.e., greater output of optical emissions 66. Also, longer wavelengths of optical signal 54 reduces fluorescence interference with emissions signal 66.

Spectroanalysis system 70 may include, for example, spectrometer 72 and charge coupled device camera (CCD) 74. Spectroanalysis system 70 detects the spectral characteristics of SERS optical emissions 66, which then are provided to computer 80 for recording and analysis via signal line 78. Heat exchanger 44 may be mounted on a staging apparatus 76 for positioning SERS structure 36 at selected positions or coordinates with respect to the propagation path of excitation light signal 54. Staging apparatus 76 operates under the supervision of computer 80 via signal line 75, and may be implemented as a one (X), two (X,Y), or three dimensional (X,Y,Z) positioning system, where X, Y, and Z represent coordinates on mutually orthogonal axes. Staging apparatus 76 enables SERS structure 36 to be positioned at selected coordinates.

Different analytes condense at different temperatures. Controlling the temperature of SERS structure 36 facilitates condensation of selected analytes 26 that may be present in sample chamber 33 so that they may condense onto SERS structure 36. When in contact with each other, analyte 26 and SERS structure 36 may be optically stimulated by optical excitation signal 54 to produce optical emissions 66 that are unique to a particular analyte. Such optical emissions 66 may be detected by spectroanalysis system 70 and then correlated to a particular analyte 26.

Figure 2:
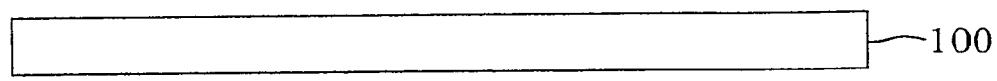
FIG. 2 shows a metal foil that from which a SERS structure is fabricated.
Figure 3:
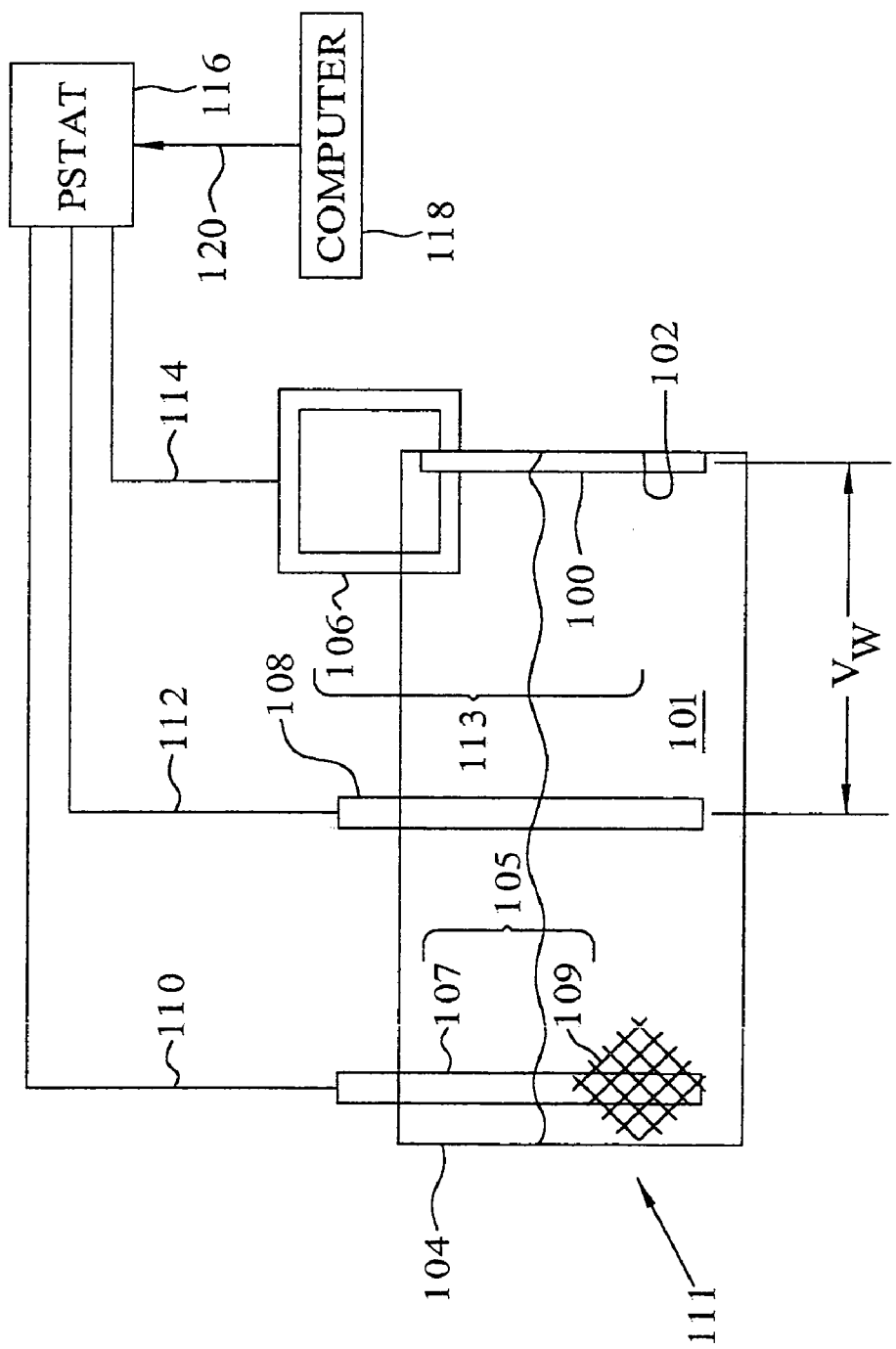
FIG. 3 represents a system for electrochemically etching the metal foil depicted in FIG. 2.

SERS structure 36 is manufactured from metal foil 100, as shown in FIG. 2, that, for example, may have a thickness in the range of about 0.25 to 0.5 mm and consist essentially of a metal selected from the group that includes gold, copper, and silver, as well as alloys that may include any of these metals. Foil 100 is subjected to an electrochemical etch as described with reference to FIG. 3, wherein foil 100 is shown to be partially immersed in an electrochemical cell 111 that includes electrolyte 101, such as a 0.1M solution of potassium chloride (KCl) held within fluid container 101, electrodes 105 and 108, and a working electrode 113 comprised of clamp 106 and foil 100. Foil 100 is clamped to side 102 of fluid container 104 by metallic clamp 106 so that there is electrical continuity between clamp 106 and foil 100. Metallic clamp 106 should not be immersed in the electrolyte 101 in order to prevent metallic ions from the clamp 106 from contaminating the electrolyte 101. Also immersed in electrolyte 101 are counter electrode 105 and reference electrode 108. Counter electrode 105 preferably is made of platinum wire 107 and platinum gauze 109 that is electrically and mechanically coupled to wire 107. Electrode 105 is positioned so that gauze 109 is immersed in electrolyte 101 to increase the active surface area of electrode 105 in electrolyte 101. Reference electrode 108 preferably is made of silver/silver chloride. Electrodes 105 and 108, and clamp 106 are connected via wires 110, 112, and 114, respectively, to potentiostat 116. Potentiostat 116 maintains appropriate voltage levels at each of electrodes 105 and 108, and electrode 113 under the supervision of computer 118 via signal line 120.

Figure 5:
FIG. 5 shows the metal foil of FIG. 2 having a roughened surface after being electrochemically etched.
Figure 4:
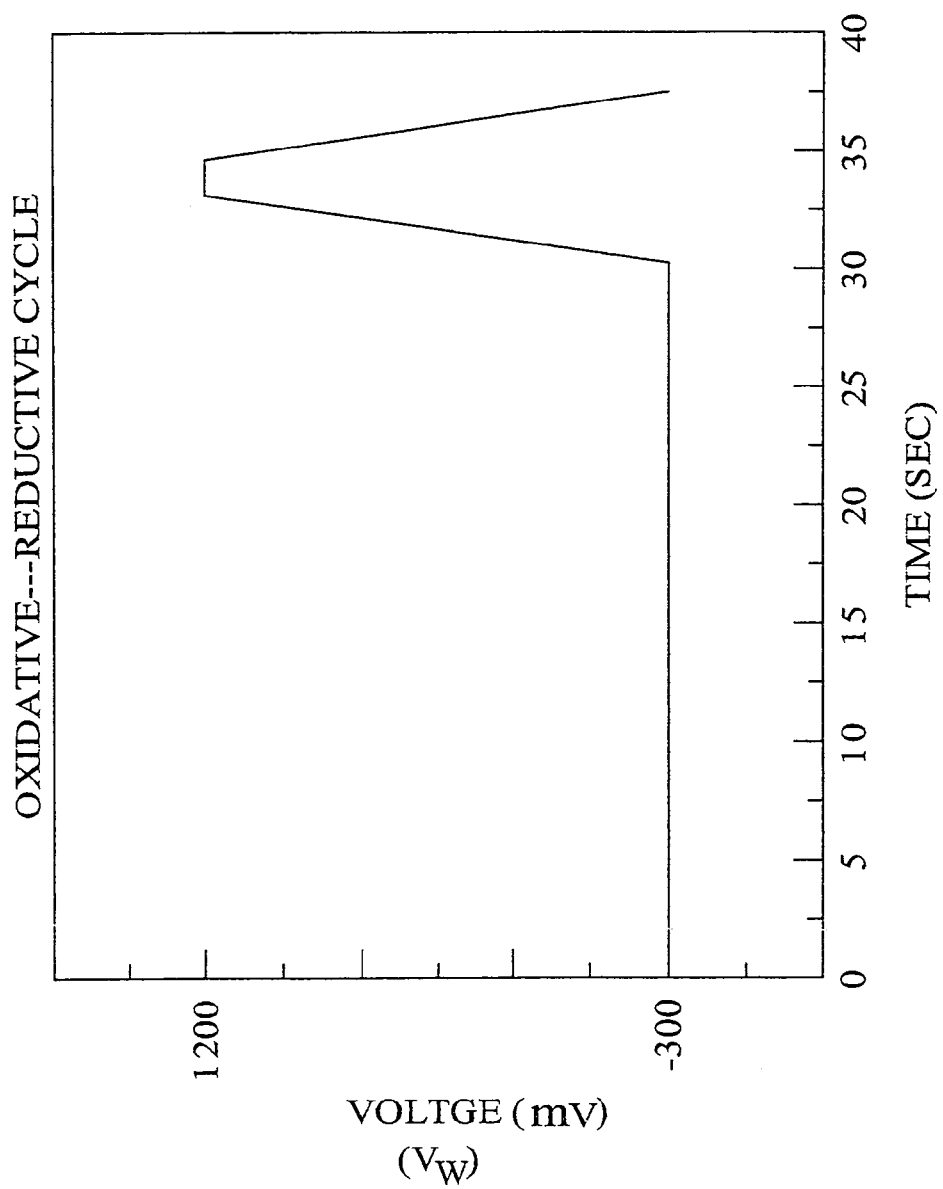
FIG. 4 graphically represents an oxidative-reductive cycle for roughening the surface of the foil shown in FIG. 2.

In the manufacture of SERS structure 36, the voltage, VW, of working electrode 113 is modulated from −300 mV to 1200 mV with respect to the voltage of reference electrode 108 for a predetermined number of oxidative-reductive cycles. An example of an oxidative-reductive cycle is shown, by way of example, in FIG. 4. In the oxidative-reductive cycle shown in FIG. 4, VW is held at −300 mV for about 30 seconds and then ramped to 1200 mV at a rate of about 500 mV/s. Next, VW is held at 1200 mV for about 1.3 seconds and then reduced to −300 mV at a rate of about −500 mV/s. Subjecting foil 100 to preferably 25 oxidative-reductive cycles of the type described above with reference to FIG. 4, provides foil 100 with a roughened metal surface 120 having an average surface roughness of about 20 Å, as shown in FIG. 5.

Figure 6:
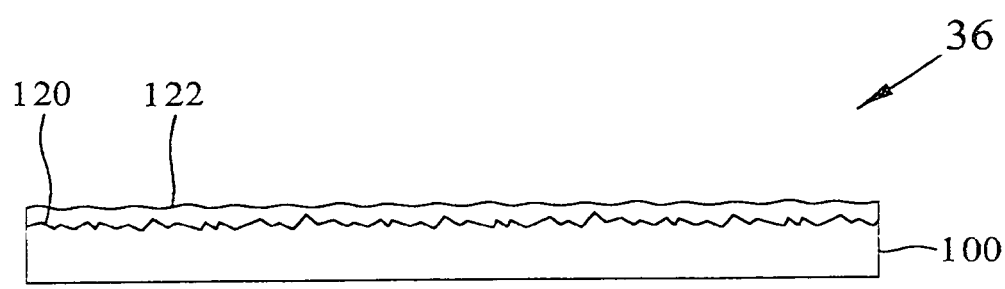
FIG. 6 represents the SERS structure manufactured from the processed metal foil depicted in FIG. 5.

Foil 100 then may be placed in a dilute, as for example, 10-3 M, ethanolic thiol solution at ambient temperature and pressure and allowed to soak for a period of time, such as 24 hours. Suitable thiols include aliphatic, aromatic, alcohol, and ether organic molecules. Soaking foil 100 in the thiol solution provides time for the roughened metal surface 120 to react with the thiol to form a durable, self-assembled monolayer 122 on roughened metal surface 120 as shown in FIG. 6. Thus, foil 100 is transformed into SERS structure 36. Thiol coatings may be selected which have an affinity for the analyte (organic compounds, metal ions, or anions) of interest that may be present in gas mixture 28.

Obviously, numerous modifications and variations of the present invention are possible in light of the above teachings. It is therefore understood that within the scope of the appended claims the invention may be practiced otherwise than as specifically described herein.

We claim:

1. A thermo-electrically cooled surface enhanced Raman spectroscopy sensor chamber, comprising:
    a chamber body having a sample chamber;
    a SERS structure positioned in said sample chamber,
    wherein said SERS structure includes a self-assembled monolayer of thiol;
    a thermoelectric cooling device for cooling said SERS structure;
    a heat exchanger for removing heat energy from said sample chamber; and
    an optical module mounted to said chamber body for directing an excitation light signal to irradiate said SERS structure and for receiving a SERS optical emissions signal.

2. The sensor chamber of claim 1 that further includes a staging apparatus for positioning said SERS structure.

3. The sensor chamber of claim 1 wherein said optical emissions signal represents an analyte in contact with said SERS structure, where said analyte is selected from the group that includes benzene, toluene, ethylbenzene, MTBE, TNT, RDX, cocaine, heroin, saran, xylene, mustard gas, and chlorinated solvents.

4. The sensor chamber of claim 1 wherein said SERS structure includes a metal foil with a roughened surface, wherein said self-assembled monolayer is formed on said roughened surface.

5. The sensor chamber of claim 4 wherein said metal foil consists essentially of a metal selected from the group consisting of gold, copper, and silver.

6. A thermo-electrically cooled surface enhanced Raman spectroscopy sensor system, comprising:
    a source for providing an inert gas;
    a manifold having a semipermeable membrane for separating moisture from an analyte wherein said analyte and said inert gas mix to create a gas mixture;
    a chamber body having a sample chamber for receiving said gas mixture;
    a SERS structure is positioned in said sample chamber,
    wherein said sample chamber includes a thermoelectric cooler for cooling said SERS structure;
    wherein said SERS structure includes a metal foil having a roughened surface, and
    wherein said SERS structure further includes a self-assembled monolayer of thiol formed on said roughened surface;
    a heat exchanger for removing heat energy from said sample chamber;
    an optical energy source for generating an optical excitation signal that irradiates said SERS structure; and
    a spectroanalysis system for detecting optical emissions generated in response to said SERS structure being irradiated by said optical excitation signal when said analyte is in contact with said SERS structure.

7. The system of claim 6 wherein said optical energy source includes a laser.

8. The system of claim 7 wherein said optical excitation signal has a wavelength in the range of about 633 to 852 nm.

9. The system of claim 6 further including a staging apparatus for positioning said SERS structure at selected coordinates.

10. The system of claim 6 wherein said spectroanalysis system includes a spectrometer for detecting said spectral characteristics of said optical emissions and a CCD device for recording said spectral characteristics.

11. The system of claim 6 wherein said analyte is selected from the group that includes benzene, toluene, ethylbenzene, MTBE, TNT, RDX, cocaine, heroin, saran, xylene, mustard gas, and chlorinated solvents.

12. A thermo-electrically cooled surface enhanced Raman spectroscopy sensor system, comprising:
    a source for providing an inert gas;
    a manifold having a semipermeable membrane for separating moisture from an analyte wherein said analyte and said inert gas mix to create a gas mixture;
    a chamber body having a sample chamber for receiving said gas mixture;
    a SERS structure positioned in said sample chamber,
    wherein said SERS structure includes a metal foil having a roughened surface, and
    wherein said SERS structure further includes a self-assembled monolayer of thiol formed on said roughened surface;
    a thermoelectric cooling device for cooling said SERS structure;
    a heat exchanger for removing heat energy from said sample chamber;
    an optical energy source for generating an optical excitation signal that irradiates said SERS structure; and
    a spectroanalysis system for detecting optical emissions generated in response to said SERS structure being irradiated by said optical excitation signal when said analyte is in contact with said SERS structure.

* * * * *